(12) United States Patent
Huber

(10) Patent No.: US 11,511,005 B2
(45) Date of Patent: Nov. 29, 2022

(54) ENDOSCOPE, METHOD FOR CLEANING AN ENDOSCOPE, AND CLEANING DEVICE FOR CLEANING AN ENDOSCOPE

(71) Applicant: HOYA CORPORATION, Tokyo (JP)

(72) Inventor: Harald Huber, Augsburg (DE)

(73) Assignee: HOYA CORPORATION, Tokyo (JP)

( * ) Notice: Subject to any disclaimer, the term of this patent is extended or adjusted under 35 U.S.C. 154(b) by 449 days.

(21) Appl. No.: 16/475,200

(22) PCT Filed: Feb. 12, 2018

(86) PCT No.: PCT/IB2018/000095
§ 371 (c)(1),
(2) Date: Jul. 1, 2019

(87) PCT Pub. No.: WO2018/150252
PCT Pub. Date: Aug. 23, 2018

(65) Prior Publication Data
US 2019/0351081 A1    Nov. 21, 2019

(30) Foreign Application Priority Data

Feb. 14, 2017 (DE) .......................... 102017102871.4

(51) Int. Cl.
*A61L 2/08* (2006.01)
*A61L 2/10* (2006.01)
(Continued)

(52) U.S. Cl.
CPC ................. *A61L 2/088* (2013.01); *A61L 2/10* (2013.01); *A61L 2/232* (2013.01); *A61L 29/106* (2013.01);
(Continued)

(58) Field of Classification Search
CPC ............. A61L 2/088; A61L 2/10; A61L 2/232
See application file for complete search history.

(56) References Cited

U.S. PATENT DOCUMENTS 7,744,555 B2    6/2010    Dimauro et al.
8,591,406 B2    11/2013   Hirayama
(Continued)

FOREIGN PATENT DOCUMENTS

JP    2000-139838 A    5/2000
WO   2012/177803 A1   12/2012

OTHER PUBLICATIONS

JP2000-139838 A—English language machine translation (Year: 2000).*

(Continued)

*Primary Examiner* — Sean E Conley
(74) *Attorney, Agent, or Firm* — Greenblum & Bernstein, P.L.C.

(57) ABSTRACT

The invention refers to an endoscope including at least one channel which may be contaminated in use, wherein the channel wall of the at least one channel is formed of a material having properties capable of photocatalysis. The invention further refers to a method for cleaning such an endoscope including the steps of:
  connecting the endoscope to a reprocessing device,
  performing a photocatalytic treatment at least in the at least one channel for the purpose of the decomposition of organic residues on the surface of the channel, and
  rinsing the endoscope.
The invention further refers to a cleaning device for cleaning such an endoscope.

9 Claims, 4 Drawing Sheets

(51) Int. Cl.
*A61L 2/232* (2006.01)
*A61L 29/10* (2006.01)
*A61L 29/12* (2006.01)
*A61L 29/14* (2006.01)
*A61B 1/12* (2006.01)

(52) U.S. Cl.
CPC ............ *A61L 29/126* (2013.01); *A61L 29/143* (2013.01); *A61B 1/121* (2013.01); *A61L 2202/11* (2013.01); *A61L 2202/17* (2013.01); *A61L 2202/24* (2013.01)

(56) References Cited

U.S. PATENT DOCUMENTS

| | | | |
|---|---|---|---|
| 2003/0125679 | A1 | 7/2003 | Kubota et al. |
| 2004/0009091 | A1* | 1/2004 | Deal .................. A61B 90/70 422/3 |
| 2010/0268151 | A1 | 10/2010 | Mauge et al. |
| 2013/0060188 | A1 | 3/2013 | Bedwell et al. |
| 2016/0246049 | A1* | 8/2016 | Sakai .................. G02B 23/2423 |

OTHER PUBLICATIONS

Derwent Abstract for KR2005080596 (Year: 2006).*
Office Action issued in Chinese Counterpart Patent Appl. No. 201880009598.7, dated Oct. 11, 2021.
Office Action issued in China Counterpart Patent Appl. No. 201880009598.7, dated Jul. 9, 2020.
Office Action issued in China Counterpart Patent Appl. No. 201880009598.7, dated Mar. 11, 2021.
International Search Report issued in WIPO Patent Application No. PCT/IB2018/000095, dated Jul. 10, 2018.
Office Action issued in German family member Patent Appl. No. 102017102871.4, dated Nov. 2, 2017.

* cited by examiner

ENDOSCOPE, METHOD FOR CLEANING AN ENDOSCOPE, AND CLEANING DEVICE FOR CLEANING AN ENDOSCOPE

The present invention relates to an endoscope comprising at least one channel which may be contaminated in use. Furthermore, the present invention relates to a cleaning method and a cleaning device for cleaning an endoscope.

An endoscope can be used for examining, for example, the esophagus, the duodenum, the bile duct, the gall bladder, the pancreatic duct, the pancreas, etc.

Such an endoscope is inserted into the patient and is advanced to the location where the desired examination is to take place.

After the endoscope has been used, it is subjected to reprocessing. Such reprocessing has to reliably prevent the transmission of all germs or microorganisms, such as bacteria, viruses, fungi, worms and spores. In the course of reprocessing, the endoscope is first cleaned manually in order to remove all traces of organic material or chemical residues. After the cleaning, the endoscope undergoes machine disinfection or sterilization. In this way, it shall be avoided that germs or microorganisms, etc., with which an endoscope has come into contact during its use, are transferred to another patient during the next use.

It is the object of the present invention to provide an endoscope in which it is prevented even more reliably that germs with which an endoscope has come into contact, are transferred to another patient during the next use. Furthermore, an improved cleaning method and an improved cleaning device for cleaning an endoscope shall be provided.

This object is achieved by an endoscope comprising the features of claim 1. An inventive method for cleaning an endoscope is shown in claim 10. An inventive cleaning device for cleaning an endoscope is shown in claim 23.

Advantageous further developments are the subject matter of the dependent claims.

In the invention, an endoscope comprises at least one channel which may be contaminated in use. The channel wall of the at least one channel is formed of a material having properties capable of photocatalysis.

In such an endoscope, a photocatalytic process at the channel wall can be effected by a simple UV treatment, i.e. an exposure to UV light. During this photocatalytic process, radicals are formed from water or air. These radicals, in turn, oxidatively decompose microbiological contaminants.

The channel wall of the at least one channel can be made of plastic to which a photocatalyzable substance is added. In this way, the photocatalyzable substance can be integrated in the material of the channel wall.

The channel wall of the at least one channel can be made of plastic which is compounded with a photocatalyzable substance. During compounding, treatment of plastic takes place by admixing additional substances (fillers, additives, etc.) so as to achieve desired properties. Compounding can take place in an extruder to which the selected additive is added through a feed opening and in which the plastic is uniformly mixed with the additive. In this way, it can be achieved that the photocatalyzable substance is uniformly distributed in the plastic.

Alternatively, the channel inner wall of the at least one channel can be coated with a photocatalyzable substance.

The material having properties capable of photocatalysis may be a material which also has hydrophilic properties. These hydrophilic properties result in that on the surface of the channel inner wall, a water layer is formed by which impurities can easily be removed. Thus, a self-cleaning, dirt-removing surface is provided which is highly advantageous during endoscopic use.

The photocatalyzable substance can be titanium oxide.

In particular, the photocatalyzable substance can be titanium oxide in anatase modification.

Furthermore, the photocatalyzable substance can be titanium oxide in an anatase-rutile mixture.

A UV stabilizer and/or a thermostabilizer can be added to the photocatalyzable substance.

The channel wall of the working channel can be formed elastically.

The plastic of the at least one channel can be flexible polyether ether ketone or polyamide. Such a channel has the necessary combination of flexibility and rigidity.

The inventive method for cleaning an endoscope comprises the following steps:

connecting the endoscope to a reprocessing device, performing a photocatalytic treatment at least in the at least one channel for the purpose of the decomposition of organic residues on the surface of the channel, and rinsing the endoscope.

The photocatalytic treatment can be performed by at least guiding a UV probe through the at least one channel.

The UV probe may be a UV-A probe.

The inventive cleaning device for cleaning an endoscope comprises an integrated UV probe for performing a photocatalytic treatment.

The endoscope can be a duodenoscope. However, the endoscope can also be any other endoscope. Every endoscope has channels which can be designed in accordance with the invention so as to allow microbiological contaminants to be decomposed better.

The above-described aspects of the present invention can be combined appropriately.

Figure 1:
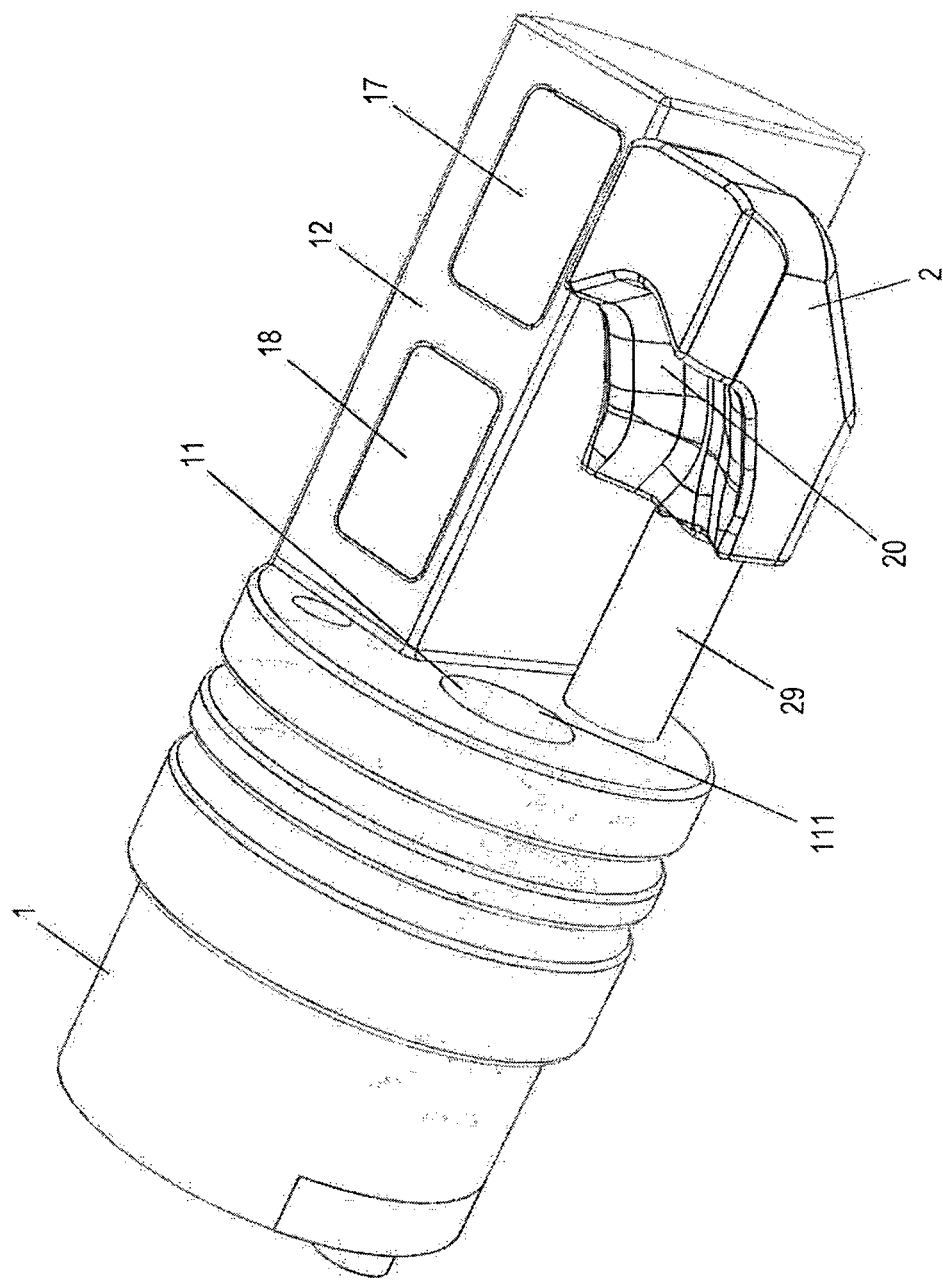
FIG. 1 shows a schematic perspective view of an endoscope head of an embodiment according to the present invention.

In the following, the present invention is described in detail by means of embodiments while referring to the drawings.

FIRST EMBODIMENT

In the following, a first embodiment of the present invention is described while referring to FIG. 1.

First of all, an inventive endoscope head 1 of a duodenoscope is described while referring to FIG. 1.

The endoscope head 1 of the endoscope according to the invention is formed as a cylindrical body and comprises a working channel 11 which extends along the longitudinal direction of the endoscope head 1. Micro-tools for examining, for example, the esophagus, the duodenum, the bile duct, the gall bladder, the pancreatic duct, the pancreas, etc. are guided in the working channel 11.

On the distal side, the endoscope head 1 includes an optical system extension 12 at which an illumination means 17 and a camera 18 are provided in the known manner, with this optical system extension 12 being shown on the righthand side in FIG. 1. The optical system extension 12 forms a flank portion having a camera and illumination. In other words, the optical system extension 12 is a housing projection with camera and illumination. This housing projection is arranged laterally adjacent to an Albarran lever 2 so that the position and the manipulating movements of the micro-tool are well in the field of vision of the camera 18.

The working channel 11 ends in a portion of the endoscope head 1 which is spaced apart from the distal end where it forms a distal outlet opening 111 of the working channel 11.

Distally of the distal outlet 111 of the working channel 11, the Albarran lever 2 which can be moved relative to the endoscope head 1 is arranged. Thus, the working channel 11 extends in the distal direction towards the Albarran lever 2.

The Albarran lever 2 comprises a tool guiding surface 20 with which a micro-tool guidable through the working channel 11 of the endoscope head 1 can make contact for being deflected in the lateral direction of the endoscope head 1 (in FIG. 1 upwards) so that the micro-tool can, for example, be inserted into a bile duct. The tool guiding surface 20 is arranged opposite to the distal end opening 111 of the working channel 11, see FIG. 1.

The Albarran lever 2 is connected to the endoscope head 1 by a connecting piece 29. The connecting piece 29 can be a pipe section in which a pulling wire anchored to the Albarran lever 2 is guided; upon actuation on the proximal side of the endoscope, this pulling wire is pulled and, thus, pivots the Albarran lever 2.

The working channel 11 is formed as a tubular or pipe-shaped element arranged in the endoscope and extending to the distal end of the endoscope head 1. This tubular or pipe-shaped element is elastic so as to allow bendings of the endoscope and follow these bendings. Furthermore, this tubular or pipe-shaped element has a channel wall. The inner circumferential surface of the channel wall faces the micro-tool that is being guided through.

The working channel 11, i.e. the tubular or pipe-shaped element, is made of plastic, such as flexible polyether ether ketone or polyamide. These are merely examples. Other plastics can be used, as well.

A photocatalyzable substance is admixed to the plastic. Thus, a working channel 11 can be formed by producing the tubular or pipe-shaped element by means of extruding the plastic material mixed with the photocatalyzable substance.

As a photocatalyzable substance, titanium dioxide (titanium (IV) oxide) can be used, for example.

Titanium dioxide occurs naturally in the three modifications rutile, anatase and brookite.

Titanium dioxide in rutile modification has conventionally been used e.g. as color additive in plastics technology.

Compared to the rutile modification, titanium dioxide in anatase modification has a higher photoactivity. This property of the anatase modification is, in accordance with the invention, used for photocatalysis (photo-oxidation). Titanium dioxide in anatase modification has so far been used e.g. for wall colors to decompose contaminants, such as nicotine smoke, soot or algae.

During photocatalysis, by exposure to ultraviolet light, cell wall-damaging radicals are formed at the working channel 11, the radicals effectively killing microorganisms. Thus, the working channel 11 designed in accordance with the invention has an anti-microbial effect.

By exposure to energy-rich ultraviolet light, electrons are lifted to a higher energy level and, via oxygen vacancies, can diffuse to the surface of the titanium dioxide where they form, together with molecules, the above-mentioned radicals. In the presence of water or air humidity in the working channel 11, redox reactions occur, during which reactive oxygen species (ROS) can be formed. The resulting radicals are particularly reactive.

Another effect of the titanium dioxide that is used in accordance with the invention is the strong hydrophilic (superhydrophilic) property with extremely small surface contact angles, caused by UV radiation. In this way, no droplets but a thin water layer is formed on the surface in the working channel 11. Thus, the channel inner wall of the working channel 11 becomes a superhydrophilic surface. This hydrophilic property occurs only after activation with UV radiation. In this way, water-wetting properties are imparted to the surface in the working channel 11. This facilitates the removal of dirt particles and harmful microorganisms from the working channel 11.

These photocatalytic effects of the titanium dioxide are now inventively used in the working channel 11. In particular, titanium dioxide in anatase modification is admixed to the plastic for the working channel 11 as an additive; in this way, a so-called compound is formed. During this compounding, a photocatalytic property is imparted to the plastic (e.g. flexible polyether ether ketone or polyamide).

Apart from the admixing of titanium dioxide in anatase modification, a UV stabilizer and/or a thermostabilizer can also be added during compounding of the plastic (e.g. flexible polyether ether ketone or polyamide).

The UV stabilizer protects the plastic from ageing through ultraviolet radiation. The kind of the UV stabilizer is not restricted. Any UV stabilizer can be added to the plastic as additive, as long as it is suitable for the application in an endoscope.

The thermostabilizer protects the plastic against the harmful effect of high temperatures. The kind of the thermostabilizer is not restricted. Any thermostabilizer can be added to the plastic as additive, as long as it is suitable for the application in an endoscope.

Titanium dioxide in anatase modification is relatively expensive compared to titanium dioxide in rutile modification. For lowering the costs of the added material, titanium dioxide in anatase modification can be diluted by means of titanium dioxide in rutile modification. In this way, the costs can be lowered if titanium dioxide in rutile modification is additionally admixed to the titanium dioxide in anatase modification.

Thus, as an alternative, a mixture of titanium dioxide in anatase modification and titanium dioxide in rutile modification can be admixed to the plastic for the working channel 11. A UV stabilizer and/or a thermostabilizer can be added to this mixture, too.

The channel wall of the working channel 11 therefore has a property capable of photocatalysis. Thus, by the application of ultraviolet radiation, dirt particles and harmful microorganisms can more easily and more efficiently be removed from the working channel 11.

SECOND EMBODIMENT

In the following, a second embodiment of the present invention is described.

In the first embodiment, the working channel 11, i.e. the tubular or pipe-shaped element, is made of plastic (e.g. flexible polyether ether ketone or polyamide) into which titanium oxide is admixed as a photocatalyzable substance.

On the other hand, in the second embodiment, the working channel 11, i.e. the tubular or pipe-shaped element, is made of plastic (e.g. flexible polyether ether ketone or polyamide) without titanium oxide being admixed.

Instead, the channel inner wall of the working channel 11 is coated with the photocatalyzable substance. Any suitable coating method (e.g. immersion) can be applied.

The same titanium oxide compounds as in the first embodiment can be used for the photocatalyzable substance.

The resulting effects and advantages are the same as in the first embodiment.

THIRD EMBODIMENT

In the first embodiment, the working channel 11 is provided with titanium oxide as a photocatalyzable substance. The invention can be applied in each channel of an endoscope.

In the present third embodiment, for example, at least one jet channel 31 is provided with titanium oxide as a photocatalyzable substance.

Furthermore, the third embodiment relates to a specific cleaning device 40 for cleaning an endoscope.

In the following, the cleaning device 40 is described while referring to FIGS. 2 to 4.

Figure 2:
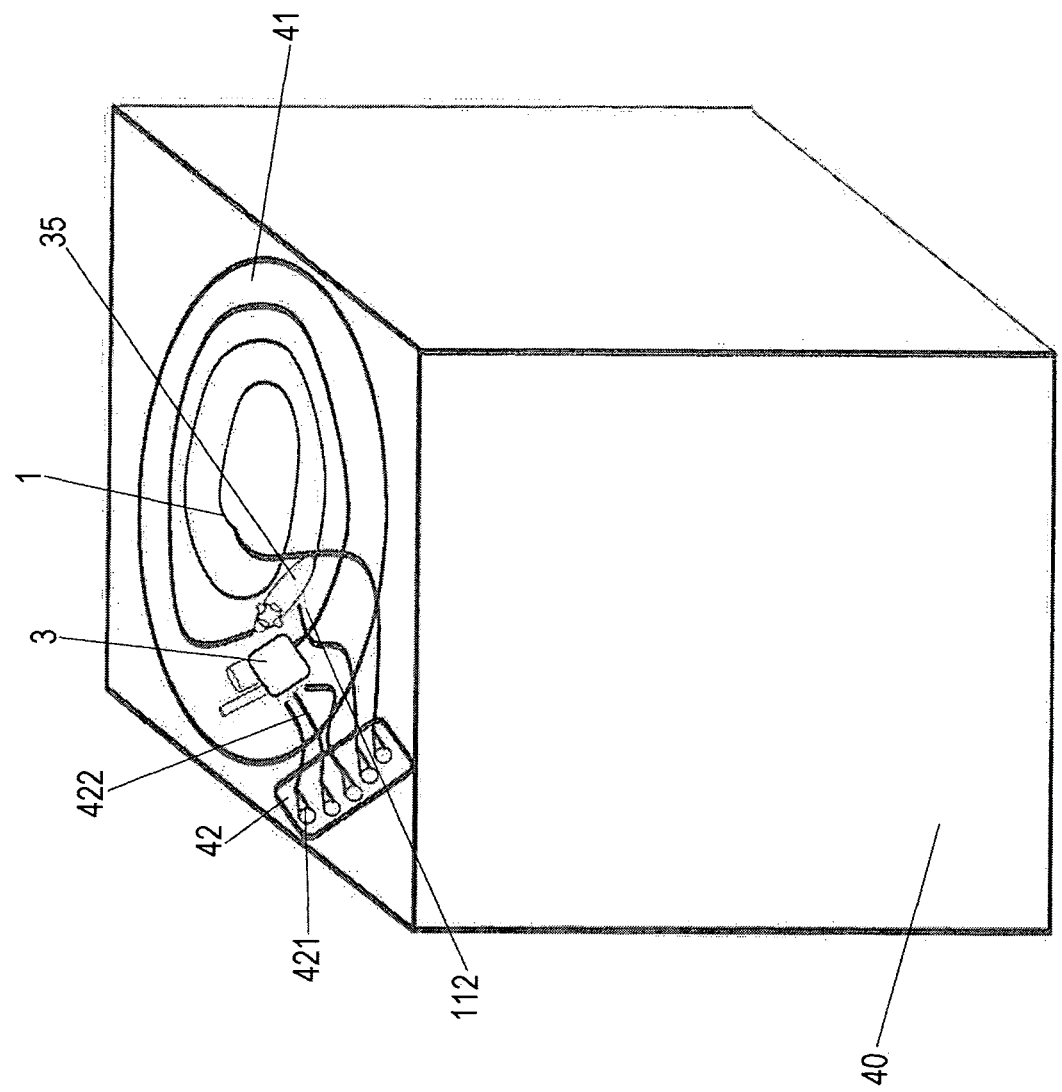
FIG. 2 shows a schematic perspective view of a cleaning device according to the present invention.
Figure 3:
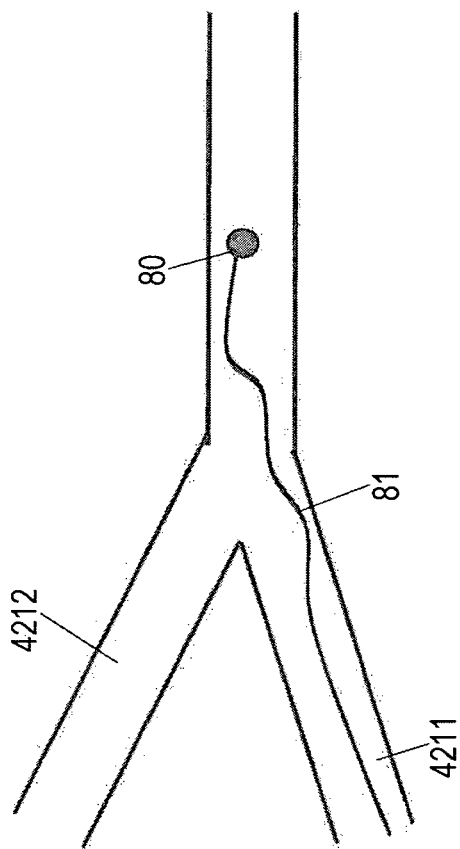
FIG. 3 schematically shows a detail of the cleaning device.

FIG. 2 shows a schematic perspective view of a cleaning device of the present invention.

A cleaning device 40 is formed as a box-like structure and, on its upper side, comprises a known cleaning vessel 41 and a media supply unit 42.

The cleaning vessel 41 is constructed as known from the prior art. An endoscope can be put into the cleaning vessel 41 in the known manner, i.e. in a spiral fashion. In the cleaning vessel 41, the endoscope that has been put therein is, for example, subjected to a photocatalytic treatment, a rinsing process, a disinfection process, etc.

The media supply unit 42 is also provided on the upper side of the cleaning device 40. The media supply unit 42 comprises a plurality of adaptors 421 which can be connected to respective terminals, i.e. at the respective channel openings of an endoscope. In FIG. 2, five adaptors 421 are shown as an example. These adaptors 421 supply air, compressed air, water, rinsing water, disinfectant, etc. to the connected endoscope. Moreover, the media supply unit 42 is constructed such that at each of the adaptors 421, it provides an inlet for a UV probe 80. More precisely, each adaptor 421 has an inlet 4212 for liquid or air media and an inlet 4211 for the UV probe 80. Here, as is shown in FIG. 3, the respective adaptor 421 can have a Y-like structure where the inlet 4212 for liquid or air media and the inlet 4211 for the UV probe 80 open into a common inlet. The common inlet is connected to a supply tube which is connected to the working channel, air/water channel, or jet channel.

The UV probe 80 preferably is a UV-A probe. This UV probe 80 is anchored to an actuating unit (not shown) of the cleaning device 40 via a flexible cable 81. The UV probe 80 may also be integrated otherwise at the cleaning device 40.

Thus, as is shown in FIG. 2, five supply tubes 422 are, for example, provided at the media supply unit 42.

In the present third embodiment, these supply tubes 422 are provided as supply tube 4221 for the jet channel 31, as supply tube 4222 and as supply tube 4223 for the air-water channel 32, as supply tube for a proximal outlet 112 of the working channel 11, and as supply tube for a distal end of the endoscope (e.g. the distal end of the working channel 11 of FIG. 1).

In the following, the application of the cleaning device according to the invention and the cleaning method are described.

After use, an endoscope according to the invention is put into the cleaning vessel 41 of the cleaning device 40, as is shown in FIG. 2. The endoscope plug 3 is connected to the corresponding supply tubes 422. In the present example, the terminal end of the supply tube 4221 is connected to the jet channel 31 of the endoscope plug 3, the terminal end of the supply tube 4222 and the terminal end of the supply tube 4223 are connected to the proximal opening of the air-water channel 32 of the endoscope plug 3, as is shown in FIG. 4. Furthermore, the terminal end of the supply tube for a proximal outlet 112 of the working channel 11 is connected to the proximal end 112 of the working channel 11 at the endoscope control body 35. Moreover, the terminal end of the supply tube for a distal end of the endoscope is connected to the distal end of the working channel 11, as is shown in FIG. 2. The endoscope plug 3 has a cable 30 by which it is connected to the endoscope control body 35.

Now, photocatalytic treatment is carried out. In this regard, the UV probe 80 is advanced in the media supply unit 42 via the respective inlet 4211 of the respective adaptor 421. A propulsion means integrated in the UV probe 80 and actuated via the cable 81 ensures forward movement of the UV probe 80.

Figure 4:
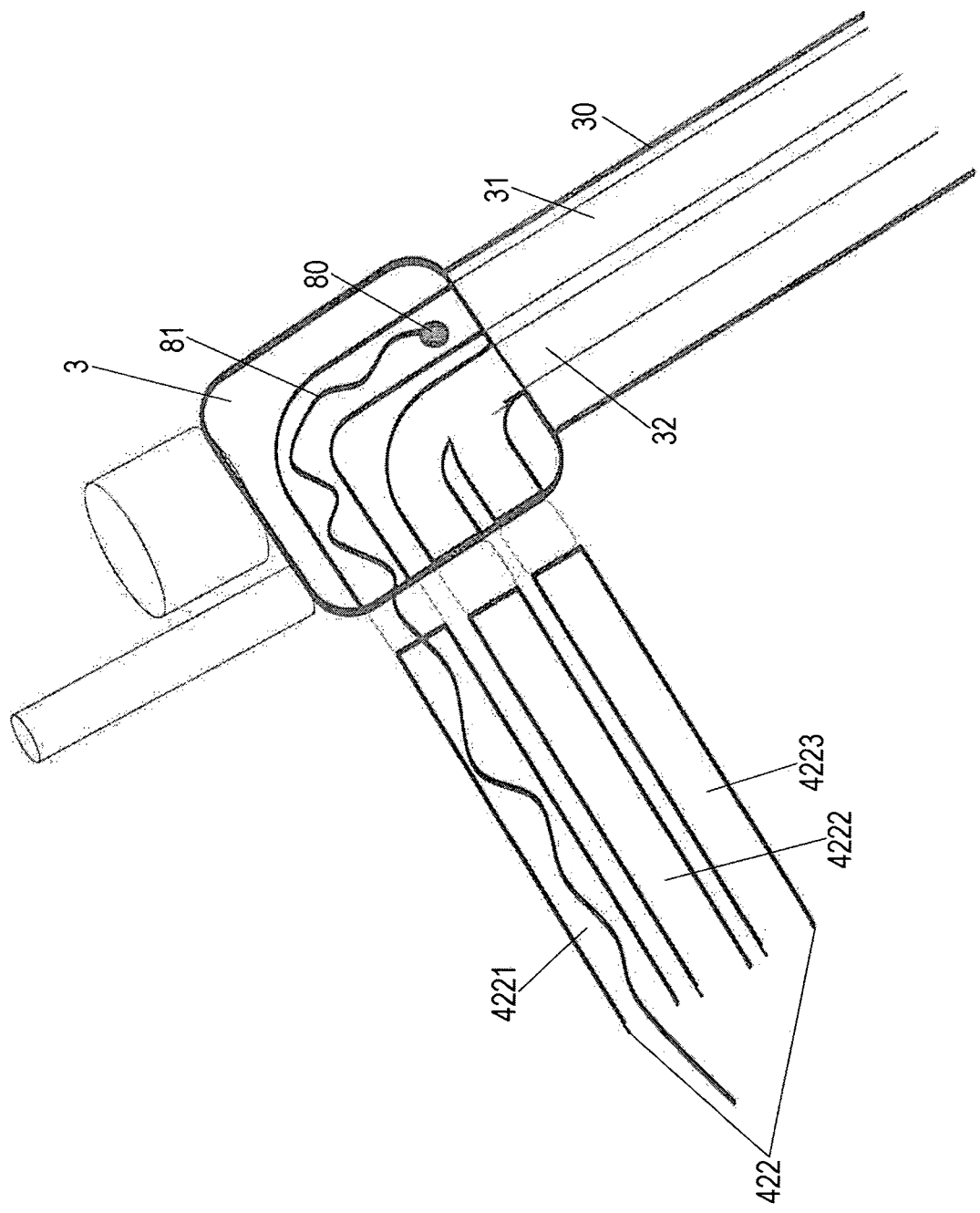
FIG. 4 schematically shows a detail of an endoscope connected to the cleaning device.

In FIG. 4, it is shown how the UV probe 80 is moved forwards in the jet channel 31 of the endoscope plug 3. In accordance with the invention, this jet channel 31 is provided with the photocatalyzable substance, as is described in embodiment 1. As soon as the UV probe 80 has reached the jet channel 31, the UV probe 80 is activated and UV-A radiation is permanently emitted. In the activated state, the UV probe 80 is moved through the entire jet channel 31. At the end of the jet channel 31, the UV probe 80, in the activated state, is again moved back through the entire jet channel 31. Alternatively, the UV probe 80 can only be active during the forward movement.

By emitting the UV-A radiation onto the channel wall of the jet channel 31 provided with the photocatalyzable substance, microbiological contaminants are oxidatively decomposed by photocatalysis. In this way, organic residues on the channel surface are decomposed. The photocatalytic treatment can be carried out appropriately in all or in selected channels of the endoscope.

Subsequent to the photocatalytic treatment, the endoscope is rinsed.

In the media supply unit 42, a rinsing medium is introduced into the appropriate channel of the endoscope via the respective inlet 4212 of the respective adaptor 421.

Subsequent to the rinsing process, the endoscope is disinfected.

In the media supply unit 42, a disinfectant medium is introduced into the appropriate channel of the endoscope via the respective inlet 4212 of the respective adaptor 421.

Thus, microbiological residues can be removed from the endoscope in a particularly advantageous manner.

Further Alternatives

The Albarran lever 2 can be omitted. The invention can also be applied to endoscopes without an Albarran lever.

In the embodiments, the term "titanium oxide" means titanium dioxide (titanium (IV) oxide). The invention is not restricted to titanium dioxide (titanium (IV) oxide). For example, also titanium (II) oxide which is activated by heating can be applied. When heated in air, titanium (II) oxide transforms to other titanium oxides depending on the temperature. Thus, titanium (IV) oxide results when the temperature is 350° C. or higher.

The invention is not restricted to titanium oxides as such, either. Any suitable photocatalyzable substance can be used.

In the embodiments, the working channel 11 or jet channel 31 or air-water channel 32 is provided with titanium oxide as a photocatalyzable substance. The invention is not restricted thereto. For example, the following channels can, in accordance with the invention, be provided with a photocatalyzable substance:

a water channel which, for example, conducts water for flushing a camera window free;

a suction channel through which liquids sucked away are conducted into the proximal direction;

a pulling wire channel through which a pulling wire is guided which actuates an actuatable element (e.g. the Albarran lever);

an air channel which conducts air into the distal direction;

a biopsy channel through which biopsy specimens that have been taken are conducted into the proximal direction;

a combined water-air channel which conducts both water and air;

a water jet channel as additional rinsing channel.

The above list merely comprises examples and is not to be understood as a limitation. Any channel of the endoscope which may be contaminated in use can be provided with titanium oxide as a photocatalyzable substance.

In the third embodiment, the UV probe 80 is activated when it has reached the corresponding channel, and UV-A radiation is permanently emitted. Alternatively, UV-A radiation can be emitted intermittently. A control can be applied, during which the UV probe 80 is activated when it has reached the corresponding channel so as to emit UV-A radiation for a predetermined period of time. Thereafter, the UV probe 80 is turned off and advanced for a predetermined distance, and is activated again so as to emit UV-A radiation for a predetermined period of time.

The invention can be applied in a duodenoscope. The principle of the invention can also be applied in an ultrasound endoscope and in any other kind of endoscope.

In the embodiments, a UV probe 80 is guided through a channel which comprises a photocatalyzable substance so as to perform a photocatalytic treatment for the purpose of the decomposition of organic residues on the channel surface. Alternatively, an appropriately strong UV source can be applied from the outside.

The invention can be used in any kind of cleaning device for endoscopes, as long as UV treatment can be applied.

LIST OF REFERENCE SIGNS 1 endoscope head
2 Albarran lever
3 endoscope plug
11 working channel
12 optical system extension
17 illumination means
18 camera
20 tool guiding surface
29 connecting piece
30 cable of the endoscope plug
31 jet channel
32 air-water channel
35 endoscope control body
40 cleaning device
41 cleaning vessel
42 media supply unit
80 UV probe
81 cable of the UV probe
111 distal outlet of the working channel
112 proximal outlet of the working channel
421 Y-adaptor of the media supply unit
422 supply tubes
4211 inlet for UV probe
4212 inlet for liquid or air media
4221 supply tube for jet channel
4222 supply tube for air for air-water channel
4223 supply tube for water for air-water channel

The invention claimed is:

1. An endoscope system comprising:
at least one channel which may be contaminated in use, the at least one channel comprising an inner wall of the at least one channel formed of a material having properties capable of photocatalysis;
an ultraviolet probe configured to move through the at least one channel and emit ultraviolet radiation that provides photocatalytic treatment of the inner wall of the at least one channel; and
at least one adaptor removably connectable to a respective said at least one channel, each said at least one adaptor having a first inlet configured to supply fluid to each respective said at least one channel, and further having a second inlet configured to accommodate the ultraviolet probe therein.

2. The endoscope system according to claim 1, wherein the inner wall of the at least one channel is made of plastic to which a photocatalyzable substance is added.

3. The endoscope system according to claim 1, wherein the inner wall of the at least one channel is made of plastic which is compounded with a photocatalyzable substance.

4. The endoscope system according to claim 1, wherein the inner wall of the at least one channel is coated with a photocatalyzable substance.

5. The endoscope system according to claim 1, wherein the photocatalyzable material is titanium oxide.

6. The endoscope system according to claim 1, wherein the photocatalyzable material is titanium oxide in anatase modification.

7. The endoscope system according to claim 1, wherein the photocatalyzable material is titanium oxide in an anatase-rutile mixture.

8. The endoscope system according to claim 1, wherein a UV stabilizer and/or a thermostabilizer are added to the photocatalyzable material.

9. The endoscope system according to claim 2, wherein the plastic is flexible polyether ether ketone or polyamide.

* * * * *